(12) United States Patent
Plott et al.

(10) Patent No.: US 11,974,757 B2
(45) Date of Patent: May 7, 2024

(54) ANTI-HEMORRHAGE DEVICE WITH RIGID BACK PLATE

(71) Applicant: THE REGENTS OF THE UNIVERSITY OF MICHIGAN, Ann Arbor, MI (US)

(72) Inventors: Jeffrey Stephen Plott, Algonac, MI (US); Kevin R. Ward, Glen Allen, VA (US)

(73) Assignee: THE REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 125 days.

(21) Appl. No.: 17/136,573

(22) Filed: Dec. 29, 2020

(65) Prior Publication Data

US 2021/0212700 A1    Jul. 15, 2021

Related U.S. Application Data

(60) Provisional application No. 62/961,415, filed on Jan. 15, 2020.

(51) Int. Cl.
| | |
|---|---|
| *A61B 17/12* | (2006.01) |
| *A61B 17/132* | (2006.01) |
| *A61B 50/30* | (2016.01) |
| *A61B 17/00* | (2006.01) |
| *A61B 50/00* | (2016.01) |
| *A61B 50/31* | (2016.01) |
| *A61B 90/00* | (2016.01) |

(52) U.S. Cl.
CPC .......... *A61B 17/1325* (2013.01); *A61B 50/30* (2016.02); *A61B 2017/12004* (2013.01); *A61B 17/12136* (2013.01)

(58) Field of Classification Search
CPC .............. A61B 17/132; A61B 17/1322; A61B 17/1325; A61B 2017/12004; A61B 2017/12022; A61B 2017/12136; A61B 17/1327; A61F 5/30
See application file for complete search history.

(56) References Cited

U.S. PATENT DOCUMENTS

| | | | | |
|---|---|---|---|---|
| 37,156 | A * | 12/1862 | Dunton .............. | A61B 17/1327 606/203 |
| 1,716,612 | A * | 6/1929 | Wing ....................... | A47B 3/14 108/34 |
| 3,625,219 | A * | 12/1971 | Abrams ............... | A61B 17/132 248/346.03 |
| 4,427,007 | A * | 1/1984 | Rexroth ............... | A61B 17/132 128/105.1 |
| 4,742,825 | A | 5/1988 | Freund et al. | |

(Continued)

OTHER PUBLICATIONS

Tanner's Select, "What is a Chamois", Aug. 27, 2018, Hopkins (Year: 2018).*

(Continued)

*Primary Examiner* — Brooke Labranche
*Assistant Examiner* — Lindsey R. Rivers
(74) *Attorney, Agent, or Firm* — MARSHALL, GERSTEIN & BORUN LLP

(57) ABSTRACT

An anti-hemorrhage device, and an anti-hemorrhage kit, includes a rigid platform and a compression device adjustably secured to the rigid platform. The kit also includes a gastroesophageal aortic occlusion device.

14 Claims, 4 Drawing Sheets

(56) References Cited

U.S. PATENT DOCUMENTS

| | | | |
|---|---|---|---|
| 6,296,654 B1 * | 10/2001 | Ward | ............... A61B 17/12136 |
| | | | 600/207 |
| 6,454,097 B1 | 9/2002 | Blanco | |
| 6,833,001 B1 * | 12/2004 | Chao | .................. A61B 17/1325 |
| | | | 606/203 |
| 2002/0016608 A1 | 2/2002 | Ward | |
| 2007/0198052 A1 | 8/2007 | Ben-David | |
| 2007/0198952 A1 | 8/2007 | Pittenger | |
| 2018/0193030 A1 | 7/2018 | Ward et al. | |
| 2018/0193032 A1 * | 7/2018 | Haeussinger | ...... A61B 17/1325 |
| 2019/0290288 A1 | 9/2019 | Popp | |

OTHER PUBLICATIONS

Written Opinion for International application No. PCT/US20/67247, dated Mar. 25, 2021.

Search Opinion for International application No. PCT/US20/67247, dated Mar. 25, 2021.

* cited by examiner

ANTI-HEMORRHAGE DEVICE WITH RIGID BACK PLATE

STATEMENT OF US GOVERNMENT SUPPORT

This invention was made with government support under Grant No. W81XWH-18-1-0033 awarded by U.S. Army Medical Research and Development Command. The government has certain rights in the invention.

FIELD OF THE DISCLOSURE

The present disclosure relates to hemorrhage occlusion devices and methods and more particularly to an anti-hemorrhage device or kit with a rigid back plate and a compression device.

BACKGROUND

Hemorrhagic shock is a leading cause of death from trauma. Many times there are delays in reaching hospitals that are qualified to take care of the complex injuries of such individuals. Many patients who die of trauma, die from multi-system involvement. Multi-system involvement may include head injury along with injuries to organs of the thoracic and abdominal cavity. Uncontrolled hemorrhage leading to hypovolemic shock is a leading cause of death from trauma especially from blunt and penetrating trauma of the abdomen. When head trauma occurs concomitantly with thoracic and abdominal hemorrhage, the brain becomes hypoperfused and, thus, becomes at greater risk for secondary injury. Currently, in the pre-hospital and emergency department setting, there are limited means to control exsanguinating hemorrhage below the diaphragm while maintaining myocardial and cerebral blood flow. Definitive control of hemorrhage is performed at surgery but this may be delayed and may not occur within the golden hour (time from injury to definitive treatment/repair) where the best opportunity lies in salvaging the patient. Survival with improved neurologic outcome might be enhanced if means were available to slow or stop ongoing hemorrhage (especially below the diaphragm) while maintaining adequate perfusion to the heart and brain until definitive treatment of the hemorrhage is available. This would be especially true of trauma victims whose transport to appropriate medical facilities would be prolonged.

One method of slowing or stopping hemorrhage is the use of a pneumatic anti-shock garment (PASG). Use of the PASG has met with varying degrees of success depending on the location of injury. This garment is placed on the legs and abdomen and is then inflated. Hemorrhage in the abdominal cavity, as well as the lower extremities, is controlled through tamponade while systemic blood pressure is raised partially through autotransfusion and by raising peripheral vascular resistance. Use of the PASG can sometimes be cumbersome and does not uniformly control hemorrhage or raise blood pressure. In addition, persons with concomitant penetrating thoracic injuries may hemorrhage more when the device is applied. The device may also raise intracranial pressure, which might detrimentally alter cerebral blood flow resulting in neurologic injury.

Other more drastic means to control abdominal bleeding prior to surgery have been the use of thoracotomy to cross-clamp the thoracic aorta and the use of balloon catheters placed into the aorta from the femoral arteries to a point above the celiac-aortic axis. These techniques have met with varying degrees of success, require a high degree of skill, and cannot be performed in hospitals not equipped to care for trauma patients or by paramedical care personnel.

Deliberately keeping hemorrhaging trauma victims in a hypotensive state is currently being examined as a means to improve survival. This is done based on the premise that overall hemorrhage (especially abdominal hemorrhage) is reduced if mean arterial pressure is kept low by not aggressively volume-repleting the victim prior to surgery. Unfortunately, this may be dangerous for trauma victims with concomitant head injury or myocardial dysfunction.

An important cause of hemorrhagic shock not caused by trauma includes rupture of abdominal aortic aneurysms. These can occur suddenly and without warning. Control of bleeding even at surgery can be difficult. Temporary measures discussed above for hemorrhage secondary to trauma have been tried for hemorrhage secondary to aneurysm rupture. The same difficulties apply. Survival might be enhanced if hemorrhage could be controlled earlier while maintaining perfusion to the heart and brain.

U.S. Pat. No. 5,531,776, and U.S. Patent Publication No. 2002/0016608, the disclosures of which are hereby incorporated herein by reference, each disclose non-invasive techniques for partially or completely occluding the descending aorta. While these techniques have been at least somewhat successful at reducing hemorrhagic shock, these methods and devices have not gained widespread acceptance due to some difficulty in advancing and properly placing the devices in a patient. Additionally, these methods require particular orientations of the devices for correct operation. Finding and maintaining the precise orientation can be difficult.

Finally, in some cases, external pressure may be necessary to stop internal or external hemorrhages. In some areas of the body, for example in the abdomen, external pressure is normally applied by hand. Hand pressure can be cumbersome and in the case where there is only one person to help, hand pressure removes one hand available to accomplish other tasks. Tourniquets may be used in some cases, but tourniquets can result in limb complications and cannot be used on the trunk of the body.

SUMMARY

In a first example, an anti-hemorrhage device includes a rigid platform and a compression device adjustably secured to the rigid platform.

In a second example, an anti-hemorrhage kit includes an anti-hemorrhage device including a rigid platform and a compression device adjustably secured to the rigid platform, and a gastroesophageal aortic occlusion device.

In yet another example, a method of stopping or slowing a hemorrhage includes placing a body part on a rigid platform, attaching a first strap to a first side of the rigid platform, attaching a second strap to a second side of the rigid platform, connecting the first and second straps to a compression device, locating the compression device over an area of hemorrhage, and operating the compression device to apply pressure to the area of hemorrhage. The first and second straps are at least partially spaced from the torso so that the torso is not fully constricted circumferentially when the compression device is operated.

Any of the first, second, and third examples may include any one or more of the following optional forms.

In one optional form, the compression device includes a pressure plate carriage and a strap carriage that is linearly translatable relative to the pressure plate carriage.

In another optional form, the pressure plate carriage and the strap carriage are connected by a screw.

In yet another optional form, the screw comprises a first screw nested within a second screw.

In yet another optional form, a pressure plate is removably attached to the pressure plate carriage.

In yet another optional form, the pressure plate has one of a generally triangular shape, a generally rectangular shape, a generally circular shape, a generally oval shape, or any combination thereof.

In yet another optional form, the rigid platform includes a first rigid housing and a second rigid housing that are pivotably connected to one another.

In yet another optional form, each of the first rigid housing and the second rigid housing include a perimeter rim that surrounds a central pocket.

In yet other optional forms, the compression device is adjustably secured to the rigid platform with a first adjustable strap and a second adjustable strap.

In yet other optional forms, the first adjustable strap is connected to the first rigid housing and the second adjustable strap is connected to the second rigid housing.

In yet other optional forms, a plurality of pressure plates is adapted to be removably secured to the compression device.

In yet other optional forms, the compression device includes a pressure plate carriage and a strap carriage that is linearly translatable relative to the pressure plate carriage.

In yet other optional forms, the pressure plate carriage and the strap carriage are connected by a screw.

DETAILED DESCRIPTION

Initially, a gastroesophageal device will be described that may be used in conjunction with an external pressure device, which will be discussed further below. The gastroesophageal device and external pressure device may be used together to slow or stop bleeding in the lower part of the body. However, each device may also be used separately to stop other types of bleeding.

Figure 1:
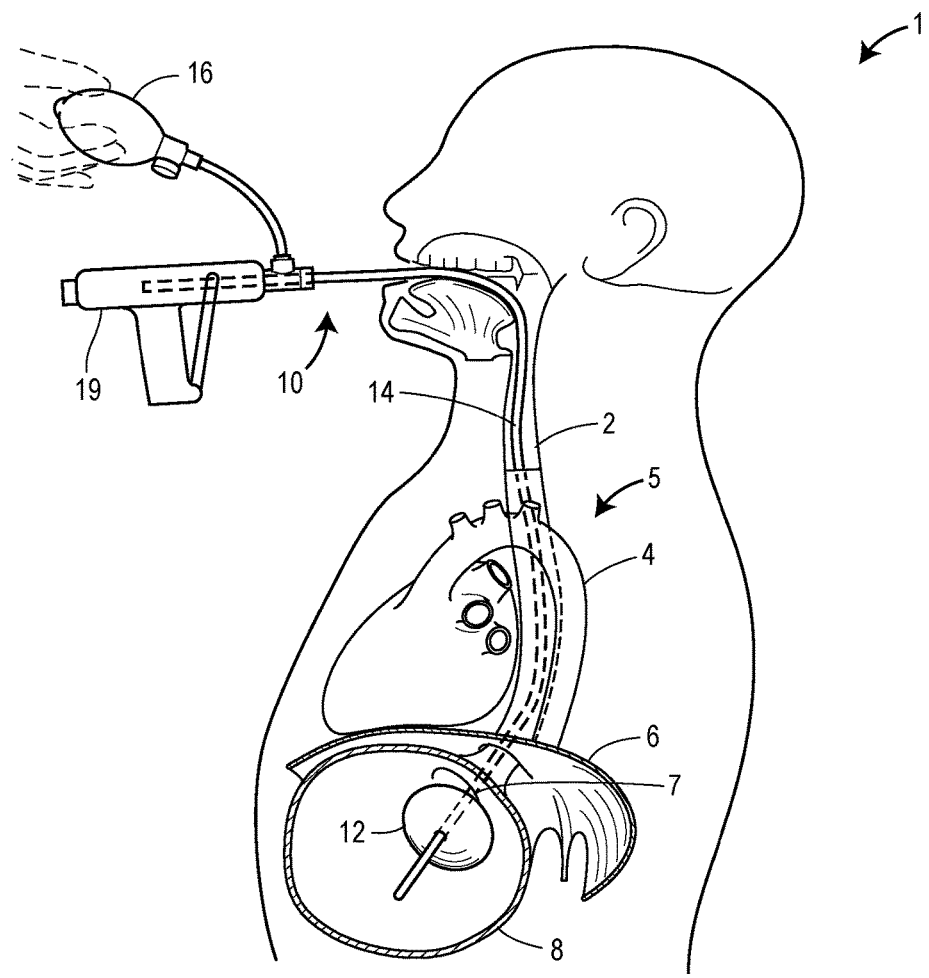
FIG. 1 is a schematic view of a gastroesophageal resuscitative aortic occlusion device inserted into a stomach of a patient.

Turning now to FIG. 1, one embodiment of a gastroesophageal resuscitative aortic occlusion device 10 is illustrated inserted into a patient 1 through the patient's esophagus 2. The patient's descending aorta 4 is juxtaposed with the esophagus 2 throughout a significant portion of the thoracic cavity 5. However, the esophagus 2 and descending aorta 4 are most closely bound where they mutually pass in close proximity through the diaphragm 6 just above the esophageal-gastric junction 7. Below the diaphragm 6, the descending aorta 4 passes posteriorly of the stomach 8 between the stomach 8 and vertebral spinal column. Because the descending aorta 4 and esophagus 2 are tightly bound in close proximity where they pass through the diaphragm 6, manipulation of a device positioned adjacent the esophageal-gastric junction 7 may be used to deflect or expand the esophagus 2 and/or the stomach 8 to thereby at least partially occlude the descending aorta 4 against the vertebral column, which decreases or stops blood flow through the descending aorta 4.

To carry out such non-invasive partial or complete occlusion of the descending aorta 4 requires proper positioning both longitudinally and radially of a surface which is moveable laterally a sufficient distance, with a sufficient force, and having a surface of sufficient area to at least partially occlude the patient's descending aorta 4. The gastroesophageal resuscitative aortic occlusion device 10 described herein overcomes the difficulties of proper positioning of the moveable surface notwithstanding the great variety in the anatomy of a patient, as will be described in more detail below.

The gastroesophageal resuscitative aortic occlusion device 10 includes a force-producing surface, such as an inflatable balloon 12, and a positioning device in the form of an elongated member, such as a catheter 14. The catheter 14 positions the inflatable balloon 12 through the patient's esophagus 2 and into a portion of the patient's stomach 8, which is near the patient's descending aorta 4. The gastroesophageal resuscitative aortic occlusion device 10 further includes an inflation mechanism, such as a hand pump 16 that selectively inflates the inflatable balloon 12. The outer surface 18 of the inflatable balloon 12 applies pressure posteriorly-laterally in the direction of the patient's descending aorta 4 sufficient to cause either partial, or substantially complete, occlusion of the patient's descending aorta 4.

Once inflated in the patient's stomach 8, proper positioning of the inflatable balloon 12 is achieved by pulling the catheter 14, such as by pulling on a handgrip 19, which draws the inflatable balloon 12 to the wall of the stomach 8 at the esophageal-gastric junction 7. The inflatable balloon 12 is drawn upwardly and posteriorly, which is the direction necessary to impinge the descending aorta 4, thereby substantially occluding blood flow through the patient's descending aorta 4.

The descending aorta 4 is a main artery of the body. As such, it is a large vessel and it is pressurized by the heart to a pressure that may extend over 200 millimeters of mercury, or approximately four pounds per square inch in some cases. Therefore, in order to substantially occlude the descending aorta 4, the gastroesophageal resuscitative aortic occlusion device 10 must overcome pressures as great as 200 mm of mercury. Furthermore, the descending aorta 4 is a muscular structure having muscle tone, which affords rigidity. Therefore, the descending aorta 4 has a stiffness which resists crushing thereof. While less than the pressure of the fluid in the descending aorta 4, this muscle tone adds appreciably to the force required to substantially occlude the descending aorta 4. In the illustrated embodiment, force sufficient to partially or completely occlude the descending aorta 4 is achieved with the inflatable balloon 12 being made of a suitable medical grade material, such as polyurethane, a polyester film, such as Mylar®, polyethylene terephthalate, or similar materials, and having a surface with an inflated diameter preferably of between approximately 3 and approximately 8 inches and most preferably between approximately 5 and approximately 7 inches. The catheter 14 is sufficiently strong to allow forces to be transmitted to inflatable balloon 12 to impart force to the surface of inflatable balloon 12 to partially or completely occlude the descending aorta 4.

Figure 2:
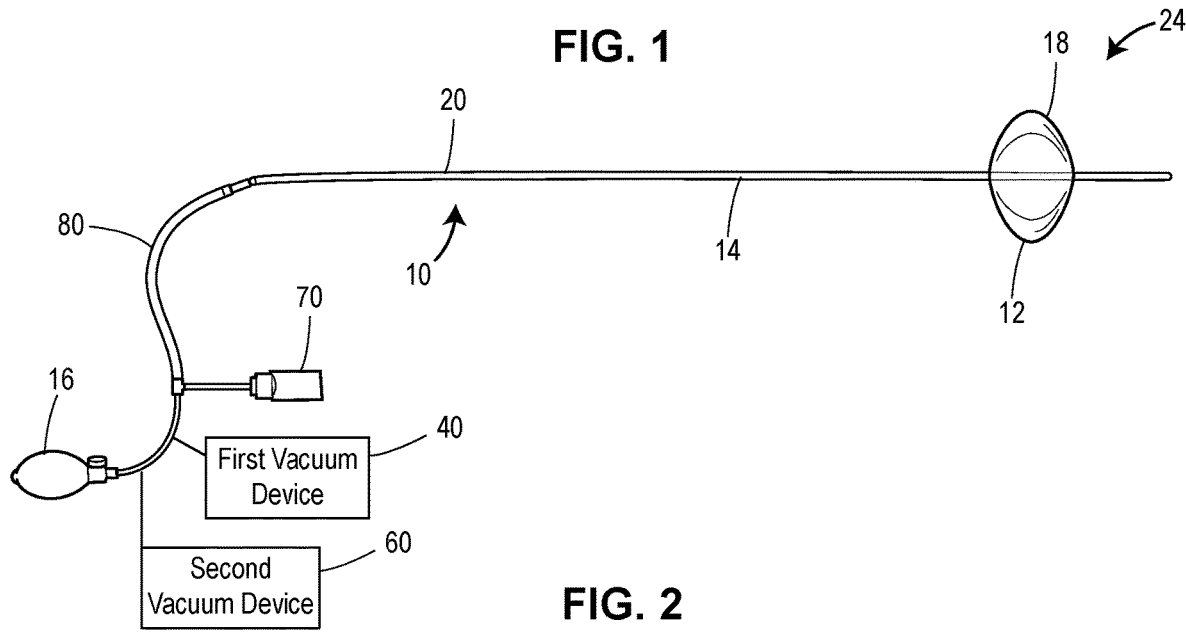
FIG. 2 is a plan view of the gastroesophageal resuscitative aortic occlusion device of FIG. 1
Figure 3:
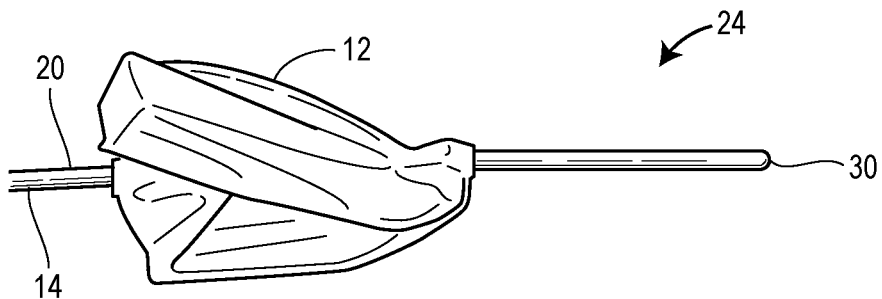
FIG. 3 is a close up view of a balloon of the gastroesophageal resuscitative aortic occlusion device of FIG. 2 in a collapsed state.
Figure 4A:
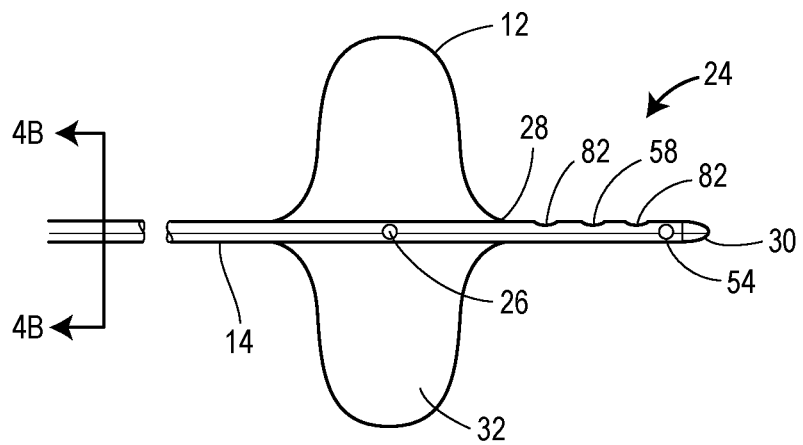
FIG. 4A is a close up view of a distal end of a catheter of the gastroesophageal resuscitative aortic occlusion device of FIG. 2.
Figure 4B:
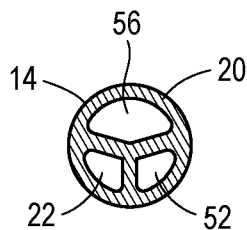
FIG. 4B is a cross sectional view of the catheter of FIG. 4A

As illustrated in FIGS. 2-4, the gastroesophageal resuscitative aortic occlusion device 10 comprises the catheter 14, which has a body 20 including a first lumen 22. The body 20 also includes a distal end 24 having a first opening 26 fluidly coupled to the first lumen 22.

The inflatable balloon 12 is disposed on the catheter 14 and a distal end 28 of the inflatable balloon 12 is displaced from a tip 30 of the distal end 24 of the catheter 14 by a distance. An interior 32 of the inflatable balloon 12 is fluidly coupled to the first opening 26.

In some embodiments, the distal end 28 of the inflatable balloon 12 is displaced from the tip 30 of the distal end 24 of the catheter 14 by at least 20 mm. In other embodiments, the distal end 28 of the inflatable balloon 12 is displaced from the tip 30 of the distal end 24 of the catheter 14 by between about 20 mm and about 150 mm, preferably by between about 30 mm and about 100 mm. Displacements in these ranges facilitate insertion and proper placement of the inflatable balloon 12 into the stomach 8.

In some embodiments, the inflatable balloon 12 comprises a material having a shore hardness of between 70A and 70D. In other embodiments, the inflatable balloon 12 further comprises a wall having a thickness of between 0.003 in and 0.015 in. These ranges of hardness and wall thickness produce sufficient force to occlude or partially occlude the descending aorta 4 when the inflatable balloon 12 is inflated.

The hand pump 16 is operably connected to the catheter 14 and fluidly coupled to the first lumen 22. Activation of the hand pump 16, such as by squeezing, forces fluid, such as ambient air, into the interior 32 of the inflatable balloon 12 under pressure through the first lumen 22 and through the first opening 26. The inflatable balloon 12 is thereby filled with fluid under pressure, which causes the inflatable balloon 12 to expand.

In some embodiments, an optional a first vacuum device 40 may be operably connected to the catheter 14, the first vacuum device 40 activating to remove fluid from the inflatable balloon 12, thereby causing the inflatable balloon 12 to deflate. The first vacuum device 40 may be fluidly connected to the first lumen 22. The first vacuum device 40 may be used to deflate the inflatable balloon 12 during insertion, repositioning, and/or during removal of the inflatable balloon 12 from the patient 1. In some embodiments, the hand pump 16 and the first vacuum device 40 may be combined into a single device, such as a hand pump with a reversible valve to allow fluid to be pumped or removed based on the valve position.

In some embodiments, the body 20 may further include a second lumen 52 and the distal end 24 of the catheter 14 may further include a second opening 54 that is fluidly coupled to the second lumen 52. The second lumen 52 may allow the second opening 54 at the distal end 24 to be fluidly connected with ambient pressure, which equalizes pressure in the stomach 8 of the patient 1 when the inflatable balloon 12 is inflated, which may prevent equalization of pressure through the esophagus 2.

In some embodiments, the body 20 may further include a third lumen 56 and the distal end 24 of the catheter 14 may further include a third opening 58, which may be fluidly coupled to the third lumen 56. The third lumen 56 may be optionally fluidly connected to a second vacuum device 60. The second vacuum device 60 may be activated to remove stomach contents when the distal end 24 is located in the patient's stomach 8. In some cases, stomach contents may need to be removed to make room for the inflatable balloon 12, or to increase effectiveness of the inflatable balloon 12, and/or to reduce the risk of patient aspiration.

In some embodiments, the gastroesophageal resuscitative aortic occlusion device 10 further includes a pressure sensor 70 that senses internal pressure in the inflatable balloon 12. The pressure sensor 70 may be fluidly connected to the first lumen 22 so that internal pressure of the inflatable balloon 12 may be sensed so that a user may inflate the inflatable balloon 12 to the proper pressure.

In yet other embodiments, the gastroesophageal resuscitative aortic occlusion device 10 may further include a pulsatile flow sensor or pressure sensor 80, either embedded into the device, or that are operatively connected to the device but that are applied external to the patient distal to the point of balloon inflation, that sense blood pressure or flow emanating from the descending aorta 4 distal to the point of balloon inflation. In some embodiments, the sensors may be separate from the balloon apparatus, but part of a larger system. The sensors provide data that enhances positioning of the balloon to aid in more complete occlusion of the descending aorta. In some uses, it may be desirable to only partially occlude the descending aorta, for example, if an operator determines that blood flow should only be slowed, but not stopped for medical reasons, in which case the sensors provide data that will assist in producing the desired amount of occlusion. In some embodiments, the sensors may comprise conductive bands or other pressure sensing elements in the balloon, or optical pressure sensors or ultrasonic pressure sensors for internal sensing, or external sensing (relative to the device itself) that may be attached to other bodily structures in the patient distal to the location of balloon inflation.

In some embodiments, the distal end 24 of the catheter 14 may include a plurality of cutouts 82 that increase flexibility of the distal end 24 to ease insertion of the catheter 14 through the esophagus 2.

In yet other embodiments, the distal end 24 of the catheter 14 may comprise a softer material than the catheter 14 proximate the inflatable balloon 12.

In some embodiments, the tip 30 of the distal end 24 of the catheter 14 comprises a blunt end.

In yet other embodiments, the gastroesophageal resuscitative aortic occlusion device 10 may comprise a removable sheath (not shown) that covers the inflatable balloon 12 during insertion of the inflatable balloon 12 through the esophagus 2. The sheath may break-away or dissolve when contacted with stomach acid to free the inflatable balloon 12 for inflation.

In yet other embodiments, the inflatable balloon 12 comprises an annular shape when fully inflated.

Turning now to FIGS. 5-8, an external pressure device 100 may be used alone, or in conjunction with the gastroesophageal resuscitative aortic occlusion device 10, to stop hemorrhages in various locations, both internal and external, on a body.

The external pressure device 100, also referred to as an anti-hemorrhage device 100, includes in one embodiment, a rigid platform 110 and a compression device 120 adjustably secured to the rigid platform 110. The compression device 120 includes a pressure plate carriage 122 and a strap carriage 124 that is linearly translatable relative to the pressure plate carriage 122. The pressure plate carriage 122 may also be considered to be linearly translatable relative to the strap carriage 124.

In some embodiments, the pressure plate carriage 122 and the strap carriage 124 are connected by a screw 126. More specifically, the pressure plate carriage 122 is connected to one end of the screw 126 so that when the screw 126 is rotated in a first direction, the pressure plate carriage 122 translates away from the strap carriage 124, and when the screw is rotated in a second direction, the pressure plate carriage translates towards the strap carriage 124. In some embodiments, the screw 126 comprises a first screw 128 nested within a second screw 130.

A pressure plate 132 is removably attached to the pressure plate carriage 122. The pressure plate 132 may have various shapes. For example, the pressure plate 132 may have any one of a generally triangular shape, a generally rectangular shape, a generally circular shape, a generally oval shape, or any combination thereof. A bottom surface of the pressure plate 132 may be shaped to fit a certain portion of the human body. For example, the bottom surface of the pressure plate 132 may be convex shaped, for example to compliment the groin area, the bottom surface of the pressure plate 132 may be concave shaped, for example to compliment a side of the leg or arm, or the bottom surface of the pressure plate 132 may be angled with respect to the pressure plate carriage 122, for example to compliment a side of the torso. In yet other embodiments, the bottom surface of the pressure plate 132 may combine any of the aforementioned shapes to better complement a location on the body having a hemorrhage. In some embodiments, the bottom surface of the pressure plate may include an absorbent layer 134 and/or may include a clotting agent to enhance blood clotting. By form fitting the bottom surface of the pressure plate 132 to the hemorrhage location, the pressure plate 132 can slow or stop bleeding more quickly, for example, by providing targeted pressure at the hemorrhage location. Additionally, the removable attachment of the pressure plate 132 to the pressure plate carriage 122 makes changing of the pressure plate 132 quick and easy. The pressure plate 132 may be removably attached to the pressure plate carriage 122 by any removable connection that provides stability to the pressure plate 132 when connected while allowing quick and easy removal from the pressure plate carriage 122. Some example removable connections include, but are not limited to, a snap-fit connection, a magnetic connection, and a removable fastener connection. A plurality of pressure plates 132 may be included in a kit with the external pressure device 100, each pressure plate 132 having a different shape, to give a user many options for selecting an optimal shape for a particular bleeding location. In some embodiments, the pressure plate 132 may include movable sections that allow the overall shape of the pressure plate 132 to be changed to better fit a bleeding location.

Figure 6:
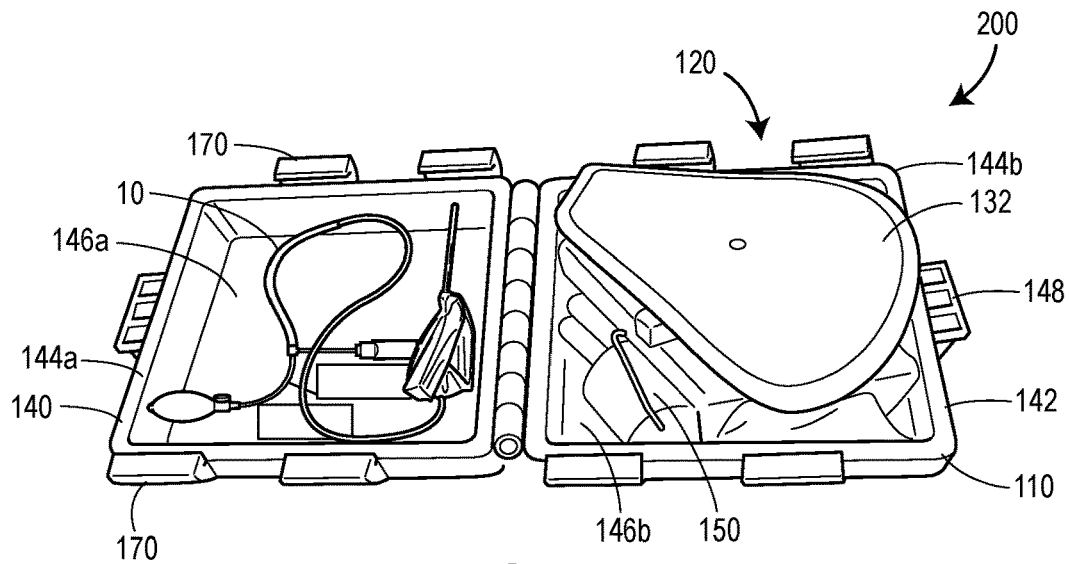
FIG. 6 is perspective view of the external pressure device of FIG. 5 stored and placed within a cavity of the rigid back plate, together with a gastroesophageal device, which forms an anti-hemorrhage kit.
Figure 7:
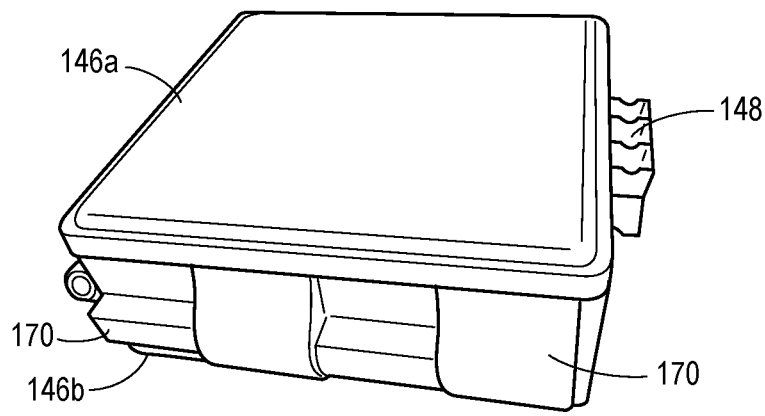
FIG. 7 is a perspective view of the external pressure device of FIG. 6 with the rigid back plate folded, thereby enclosing the external pressure device of FIG. 5 within the cavity.

The rigid platform 110 comprises a first rigid housing 140 and a second rigid housing 142 that are pivotably connected to one another, for example by a hinge. Each of the first rigid housing 140 and the second rigid housing 142 may comprise a perimeter rim 144a, 144b that surrounds a central pocket 146a, 146b (FIG. 6). The central pockets 146a, 146b form an enclosure when the first rigid housing 140 and the second rigid housing 142 are pivoted to a closed position (FIG. 7). The central pockets 146a, 146b are large enough to receive the pressure plate 132, the screw 126, the pressure plate carriage 124 and a plurality of straps 150. The central pockets 146a, 146b are also sized and shaped to receive other optional components, such as the gastroesophageal resuscitative aortic occlusion device 10 of FIGS. 1-4, and/or a plurality of pressure plates 132 having different shapes.

In an open and deployed position (FIG. 5), the first rigid housing 140 and the second rigid housing 142 form a stable platform for a portion of a body having a hemorrhage. In a closed position (FIG. 7), the first rigid housing 140 and the second rigid housing 142 form an enclosed container that protects components and devices that may be used for hemorrhage control. The enclosed container is compact and easy to carry as well as rugged and damage resistant and waterproof. The enclosed container may include one or more handles 148 to facilitate carrying of the device.

The compression device 120 is adjustably secured to the rigid platform 110 with a first adjustable strap 160 and a second adjustable strap 162. The first adjustable strap 160 is connected to the first rigid housing 140 and the second adjustable strap 162 is connected to the second rigid housing 142. The first adjustable strap 160 and the second adjustable strap 162 facilitate gross or large adjustments in the compression device 120 during initial placement of the compression device 120. The first adjustable strap 160 and the second adjustable strap 162 may include adjustment loops 164 located on the rigid platform 110 and on the strap carriage 124.

A plurality of interlocking teeth 170 may be formed on the outer side surfaces of the first rigid housing 140 and on the second rigid housing 142. The interlocking teeth 170 form stabilizing buttresses with the ground when the first rigid housing 140 and the second rigid housing 142 are in the open and deployed position (FIG. 5), and the interlocking teeth 170 align the first rigid housing 140 and the second rigid housing 142 when moving towards a closed position (FIG. 7) by interlocking with one another.

As illustrated in FIG. 6, an anti-hemorrhage kit 200 may be formed that includes the anti-hemorrhage device having the rigid platform 110 and the compression device 120, as discussed above. In some embodiments, the anti-hemorrhage kit 200 may include the gastroesophageal aortic occlusion device 10. In other embodiments, the anti-hemorrhage kit 200 may include the plurality of pressure plates 132.

Figure 5:
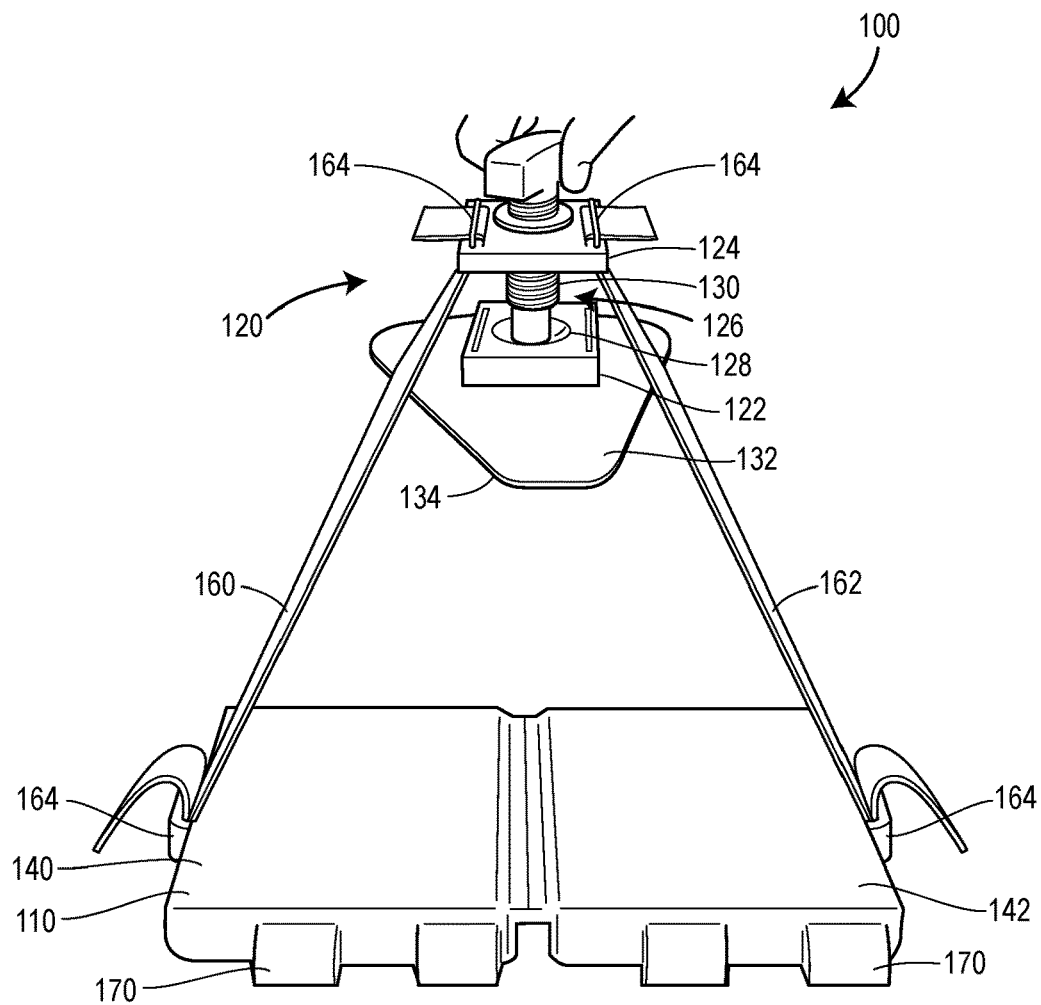
FIG. 5 is a perspective view of an external pressure device including a rigid back plate.

One method of slowing or stopping a hemorrhage on body includes procuring the kit 200 of FIG. 6 and opening the kit 200 by pivoting the first rigid housing 140 relative to the second rigid housing 142 until the central pockets 146a, 146b are exposed, thereby exposing contents stored in the central pockets 146a, 146b. The contents are removed and the rigid platform 110 is flipped over so that the central pockets 146a, 146b are facing downward, which results in a stable platform being formed for a body or body part having a hemorrhage. The first and second straps 160, 162, if not already attached, are secured to the rigid platform 110 at the adjustment loops 164, as illustrated in FIG. 5. A pressure plate 132 is then chosen based on the hemorrhage location and the pressure plate 132 is removably secured to the pressure plate carriage 122, which results in the configuration illustrated in FIG. 5.

Figure 8:
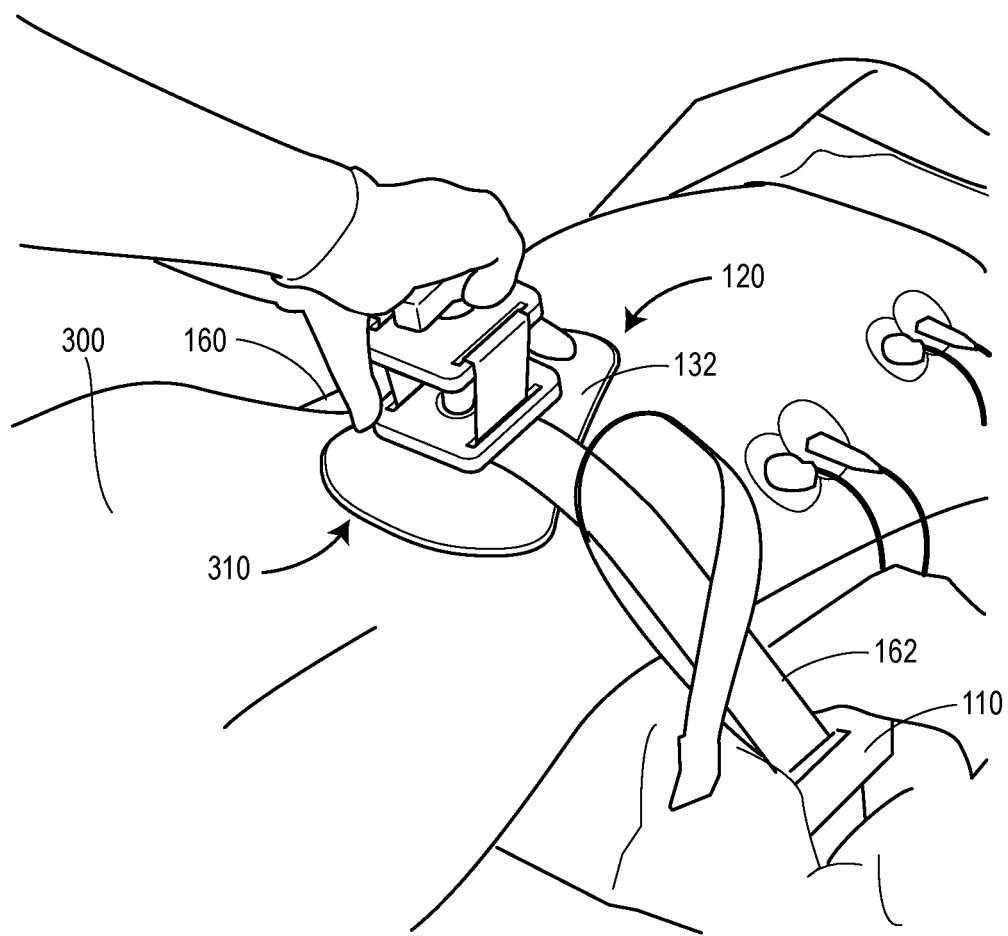
FIG. 8 is a perspective view of the external pressure device of FIG. 5 wrapped around a body part, the body part being placed on the rigid back plate.

A body part, such as a torso 300 is placed on the rigid platform 110, as illustrated in FIG. 8. The compression device 120 is located proximate an area of hemorrhage 310. The compression device 120 is operated, for example, by turning the screw 126 to move the pressure plate 132 away from the strap carriage 124, which applies pressure to the area of hemorrhage 310. The first and second straps 160, 162 are advantageously at least partially spaced from the torso 300 near the rigid platform 110 so that the torso 300 is not fully constricted circumferentially when the compression device 120 is operated. The first and second straps 160, 162 are held away from the torso by the rigid platform 110. As a result, targeted pressure is applied to the area of hemorrhage 310 while allowing blood to flow in other regions of the torso 300 not affected by the hemorrhage. In the same manner, other body parts may be placed on the rigid platform 110 to reduce or stop hemorrhages.

In one embodiment, the gastroesophageal resuscitative aortic occlusion device 10 and external pressure device 100 described above may be used in a method of occluding the descending aorta 4.

The gastroesophageal resuscitative aortic occlusion device 10 may be inserted into the stomach 8 of a patient through the esophagus 2. The hand pump 16 may be activated to pressurize the inflatable balloon 12 with a fluid. External pressure is applied to the abdomen of the patient 1 with the external pressure device 100 until blood flow through the descending aorta 4 is reduced or stopped.

The disclosed gastroesophageal resuscitative aortic occlusion device and external pressure device provide hemorrhage control for the management of trauma and an inhibition of blood flow below the diaphragm to enhance coronary and cerebral perfusion. Studies have shown that, although over half of the tissue beds are below the diaphragm, approximately two-thirds of bleeding that leads to hemorrhagic shock occurs below the diaphragm. Therefore, the ability to control bleeding below the diaphragm provides a significant advantage particularly in management of trauma. This is particularly useful in treating patients who have suffered abdominal injuries from knives and guns, blunt trauma from falls, explosions, motor vehicle accidents, complications due to the delivery of babies from subdiaphragmatic hemorrhaging and other vascular catastrophes below the diaphragm such as ruptured abdominal aortic aneurysms. The disclosed gastroesophageal resuscitative aortic occlusion device and external pressure device are particularly useful in battlefield applications in which it is essential to be able to rapidly control life-threatening hemorrhage in a non-invasive manner in order to avoid immediate death and complications from infections and the like until definitive repair of injuries can take place. Additionally, the ability to perform this procedure rapidly and effectively reduces the exposure of the medical personnel to battlefield injuries. Finally, the devices described herein may be used to elevate coronary and cerebral perfusion pressure and blood flow during cardiopulmonary resuscitation in the setting of cardiac arrest by allowing redirection of blood flow produced by chest compression to the heart and brain and away from the abdomen. Increasing coronary perfusion pressure advantageously aids in returning spontaneous circulation during cardiopulmonary resuscitation.

Changes and modifications in the specifically described embodiments can be carried out without departing from the principles of the invention. For example, electrodes can be applied to stomach balloons for use in cardiac pacing and defibrillation. Although balloons and cuffs may be inflated using air, other techniques involving hydraulic fluids and mechanical actuators may suggest themselves to those skilled in the art. Although inflatable devices are illustrated as spherical or annular, other shapes could be used such as cylindrical, pill-shaped, and the like. Also, the various elements of each illustrated embodiment of the invention can be combined and substituted with other of the embodiments. The embodiments are provided in order to illustrate the invention and should not be considered limiting. The described methods and devices are to be limited only by the scope of the appended claims.

The invention claimed is:

1. An anti-hemorrhage device comprising:
a rigid platform; and
a compression device adjustably secured to the rigid platform,
wherein the compression device comprises a pressure plate carriage and a strap carriage, the pressure plate carriage and the strap carriage being connected by a screw, the strap carriage being linearly translatable relative to the pressure plate carriage when the screw is rotated, the strap carriage being adjustably secured to the rigid platform with a first adjustable strap and a second adjustable strap, the first adjustable strap and the second adjustable strap being adjustably connected to the pressure plate carriage through an opening in the pressure plate carriage, and a pressure plate removably attached to a bottom of the pressure plate carriage.

2. The anti-hemorrhage device of claim 1, wherein the screw comprises a first screw nested within a second screw.

3. The anti-hemorrhage device of claim 1, wherein the pressure plate has a generally triangular shape.

4. The anti-hemorrhage device of claim 1, wherein the rigid platform comprises a first rigid housing and a second rigid housing, the first rigid housing and the second rigid housing being connected to one another by one of a pivotable connection, a slide connection, and a snap-fit connection.

5. The anti-hemorrhage device of claim 4, wherein each of the first rigid housing and the second rigid housing comprise a perimeter rim that surrounds a central pocket.

6. The anti-hemorrhage device of claim 4, wherein the first adjustable strap is connected to the first rigid housing and the second adjustable strap is connected to the second rigid housing.

7. The anti-hemorrhage device of claim 1, wherein the first adjustable strap is adjustably secured to the rigid platform proximate a perimeter of the rigid platform and the second adjustable strap is adjustably secured to the rigid platform proximate the perimeter of the rigid platform.

8. The anti-hemorrhage device of claim 1, wherein a bottom surface of the pressure plate is one of concave-shaped or convex-shaped.

9. The anti-hemorrhage device of claim 1, wherein a bottom surface of the pressure plate is angled with respect to the pressure plate carriage.

10. The anti-hemorrhage device of claim 1, wherein a bottom surface of the pressure plate includes an absorbent layer.

11. An anti-hemorrhage kit comprising:
an anti-hemorrhage device including a rigid platform, and a compression device adjustably secured to the rigid platform; and
a gastroesophageal aortic occlusion device,
wherein the compression device comprises a pressure plate carriage and a strap carriage, the pressure plate carriage and the strap carriage being connected by a screw, the strap carriage being linearly translatable relative to the pressure plate carriage when the screw is rotated, the strap carriage being adjustably secured to the rigid platform with a first adjustable strap and a second adjustable strap, the first adjustable strap and the second adjustable strap being adjustably connected to the pressure plate carriage through an opening in the pressure plate carriage, and a pressure plate removably attached to a bottom of the pressure plate carriage.

12. The kit of claim 11, further comprising a plurality of pressure plates that are adapted to be removably secured to the compression device.

13. The kit of claim 11, wherein the rigid platform comprises a first rigid housing and a second rigid housing.

14. An anti-hemorrhage device comprising:
   a rigid platform; and
   a compression device adjustably secured to the rigid platform,
   wherein the compression device comprises a pressure plate carriage and a strap carriage that is linearly translatable relative to the pressure plate carriage, the strap carriage being adjustably secured to the rigid platform with a first adjustable strap and a second adjustable strap, and a pressure plate removably attached to a bottom of the pressure plate carriage,
   wherein the rigid platform comprises a first rigid housing and a second rigid housing, the first rigid housing and the second rigid housing being connected to one another by one of a pivotable connection, a slide connection, or a snap-fit connection, and
   wherein the rigid housing comprises a plurality of interlocking teeth that align the first rigid housing and the second rigid housing when the first rigid housing and the second rigid housing are moved towards a closed position and the plurality of interlocking teeth form stabilizing buttresses with the ground when the first rigid housing and the second rigid housing are in an open and deployed position.

* * * * *